United States Patent
Wurm

(10) Patent No.: US 10,588,846 B2
(45) Date of Patent: Mar. 17, 2020

(54) COPOLYMERS FOR IMPROVING COLOR INTENSITY AND WASHFASTNESS OF TEMPORARY HAIR DYES

(71) Applicant: Sekisui Specialty Chemicals America, LLC, Dallas, TX (US)

(72) Inventor: David B. Wurm, Manvel, TX (US)

(73) Assignee: Sekisui Specialty Chemicals America, LLC, Dallas, TX (US)

( * ) Notice: Subject to any disclaimer, the term of this patent is extended or adjusted under 35 U.S.C. 154(b) by 139 days.

(21) Appl. No.: 15/654,269

(22) Filed: Jul. 19, 2017

(65) Prior Publication Data

US 2018/0021239 A1 Jan. 25, 2018

Related U.S. Application Data

(60) Provisional application No. 62/364,544, filed on Jul. 20, 2016.

(51) Int. Cl.
*A61Q 5/10* (2006.01)
*A61K 8/81* (2006.01)
*A61Q 5/06* (2006.01)

(52) U.S. Cl.
CPC ............ *A61K 8/817* (2013.01); *A61Q 5/065* (2013.01); *A61Q 5/10* (2013.01); *A61K 2800/4324* (2013.01)

(58) Field of Classification Search
CPC .... A61Q 5/10; A61Q 5/065; A61K 2800/882; A61K 8/8147; A61K 8/817; A61K 8/8158; A61K 2800/432
See application file for complete search history.

(56) References Cited

U.S. PATENT DOCUMENTS

| 4,182,612 A | 1/1980 | Sokol et al. |
| 6,592,632 B2 | 7/2003 | Vainshelboim et al. |
| 7,048,770 B2 | 5/2006 | Azizova et al. |
| 7,097,668 B2 | 8/2006 | Massoni |
| 2007/0107142 A1* | 5/2007 | Nguyen ............... A61K 8/64 8/405 |
| 2011/0259355 A1* | 10/2011 | Ybarra ............... A61K 8/817 132/203 |
| 2012/0110750 A1 | 5/2012 | Cremer et al. |

OTHER PUBLICATIONS

"Innovative Solutions for Hair Color Maintenance" published by HAPPI Magazine online (Dec. 1, 2008), https://www.happi.com/contents/view_features/2008-12-01/innovative-solutions-for-hair-color-maintenan/.
Basf, "Luviquat Sensation" Brochure (May 14, 2008).
Fulvio Sardo, "Shampoo Hair Coloring Compositions for Direct Dyeing of Human Hair," Journal of the Society of Cosmetic Chemists, vol. 20, No. 10, 595-602 (Sep. 16, 1969).
Gruber et al., "Examining cationic polysaccharide deposition onto keratin surfaces through biopolymer fluorescent abeling," J. Cosmet. Sci., 52, 119-129 (Mar./Apr. 2001).
Richard J. Crawford & Clarence R. Robbins, "A replacement for Rubine dye for detecting cationics on keratin," J. Soc. Cosmet. Chem., 31, 273-278 (Sep./Oct. 1980).
Robert Y. Lochhead, "The role of polymers in cosmetics: recent trends," American Chemical Society Symposium Series 961:3-56 (Apr. 2007).
Velasco et al., "Hair fiber characteristics and methods to evaluate hair physical and mechanical properties," Brazilian Journal of Pharmaceutical Sciences, vol. 45, n. 1, (Jan./Mar., 2009).

* cited by examiner

*Primary Examiner* — Eisa B Elhilo
(74) *Attorney, Agent, or Firm* — Osha Liang LLP

(57) ABSTRACT

A method for dyeing hair includes applying a polyvinyl amine copolymer solution to the hair; and applying a hair dye composition to the hair. A hair dye composition includes an aqueous base fluid; a polyvinyl amine copolymer; and an anionic or cationic hair dye. A method of making a hair dye composition includes mixing a polyvinyl amine copolymer and an anionic or cationic hair dye into an aqueous base fluid.

14 Claims, 4 Drawing Sheets
(4 of 4 Drawing Sheet(s) Filed in Color)

COPOLYMERS FOR IMPROVING COLOR INTENSITY AND WASHFASTNESS OF TEMPORARY HAIR DYES

CROSS-REFERENCE TO RELATED APPLICATION(S)

This application claims the benefit of U.S. Provisional Application No. 62/364,544 filed on Jul. 20, 2016, for "COPOLYMERS FOR IMPROVING COLOR INTENSITY AND WASHFASTNESS OF TEMPORARY HAIR DYES" by David B. Wurm, which is incorporated by reference.

BACKGROUND

Hair care products represent a large and profitable global industry that is increasingly driven by consumer demand for continual improvements in product performance. The generalized term "hair care product" covers products that serve multiple functions, sometimes at the same time, including hair cleansing, hair conditioning, hair strengthening, hair appearance enhancement, and hair dyeing/color enhancement, among others.

With respect to hair dyeing/color enhancement, the ability to evenly deposit an optimal quantity of dye onto the entirety of the hair is highly important to consumer satisfaction. This benchmark applies throughout all possible hair dyeing/color enhancement categories including: permanent dyeing, where the hair is oxidatively dyed, semi-permanent dyeing, where there is no oxidation of the dye molecules involved leading to a shorter-lived haircolor, and also in temporary hair dyes, where after the haircolor is applied it is often capable of being completely removed after as little as one wash. In the case of semi-permanent dyes, and to some extent temporary hair dyes, the dye's ability to maintain, or at least closely maintain, the original dye color during the course of its application life is often lacking. This property is often referred to as a dye's washfastness. Particularly, the dyes often lack durability and the color fades faster than desired and/or the dye may develop off-tones that are non-desirable.

Accordingly, there exists a need for new hair care compositions and components that may be used for improving the properties of hair care products.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a method for dyeing hair that includes applying a polyvinyl amine copolymer solution to the hair; and applying a hair dye composition to the hair.

In another aspect, embodiments disclosed herein relate to a hair dye composition that includes an aqueous base fluid; a polyvinyl amine copolymer; and an anionic or cationic hair dye.

In yet another aspect, embodiments disclosed herein relate to method of making a hair dye composition that includes mixing a polyvinyl amine copolymer and an anionic or cationic hair dye into an aqueous base fluid.

Other aspects and advantages of the claimed subject matter will be apparent from the following description and the appended claims.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
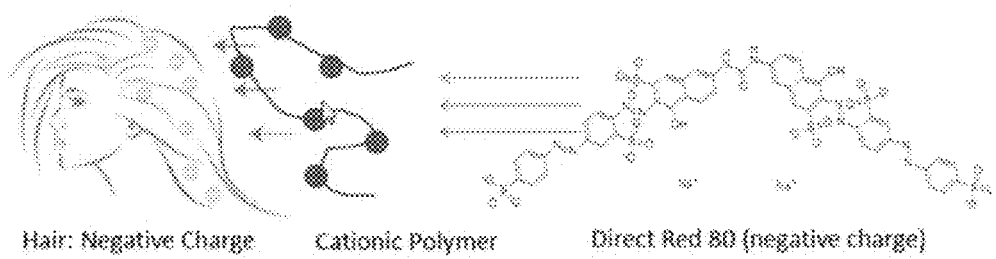
FIG. 1 is an illustration of the general steps in a Rubine Dye Test.

Embodiments disclosed herein relate generally to hair care compositions and methods of using said compositions. Embodiments of hair care compositions disclosed herein may generally exhibit improved deposition, color intensity, and washfastness when used in (or as a complement to) a variety of hair care products, particularly temporary hair dyes. Embodiments of hair care compositions disclosed herein include a copolymer including vinyl alcohol moieties or residues and vinyl amine moieties or residues, which may be referred to herein simply as the polyvinyl amine copolymer, and/or by the abbreviation PVAm.

Polyvinyl Amine Copolymer

In one or more embodiments, the polyvinyl amine copolymer includes vinyl amine residues and vinyl alcohol residues as a block copolymer, a random copolymer, or a combination thereof. In particular embodiments, a random copolymer of vinyl alcohol residues and vinyl amine residues that has been crosslinked may be particularly beneficial in forming barrier layer compositions according to the present disclosure. A process for forming the polyvinyl amine copolymer may generally include hydrolyzing a copolymer including N-vinylamide residues and one or more vinyl $C_1$-$C_{10}$ ester residues, commonly vinyl acetate residues, while dispersed in water under acidic or basic conditions. For example, U.S. Pat. No. 6,559,227, incorporated herein by reference, uses a process that may be capable of producing a suitable random polyvinylamine copolymer. In some embodiments, the N-vinylamide residues of the copolymer can be provided, for instance, from N-vinylformamide (NVF), N-vinylacetamide (NVA), and/or any suitable amide containing functional group. Production of the polyvinyl amine copolymer includes a hydrolysis step, wherein a copolymer of vinyl acetate and the N-vinylamide undergo hydrolysis to a degree of at least about 30 mol %, at least about 40 mol %, at least about 50 mol %, at least about 60 mol %, at least about 70 mol % or more, at least about 80 mol % or more, at least about 90 mol % or more, at least about 95 mol % or more, or, in some embodiments, having essentially 100% hydrolysis.

The hydrolysis of the copolymer may be carried out under acidic or basic conditions. For example, the basic conditions can be created by adding a strong alkali, such as a caustic alkali, to the hydrolysis solution. Examples of a caustic alkali include caustic soda or caustic potash. In one or more embodiments, the alkali may be added in an amount from 0.1 to 10 equivalents, such as from 0.5 to 5 equivalents per equivalent of the total monomers. In a similar way, the acidic conditions can be created by adding a suitable acid to the hydrolysis solution.

After hydrolysis, the resultant slurry may be cooled and the solid can be separated from the liquid by any suitable means. In some embodiments, the process may also include a washing step wherein the collected polymer is washed to remove any impurities. Washing can be effected with a washing liquid including at least one member selected from 1) an alcohol, 2) cold water at 20° C. or lower, or 3) salt water in order to remove the impurities in the polymer with a minimized polymer loss.

Other methods suitable for producing a polyvinyl amine copolymer that may be crosslinked according to this disclosure may be found in U.S. Pat. Nos. 5,300,566, 5,194,492, and 5,491,199.

In some embodiments, the polyvinyl amine copolymer may have the structure:

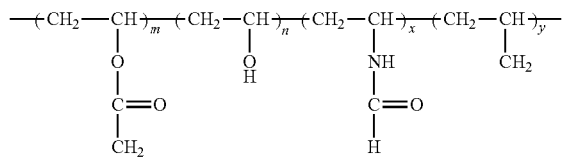

where m is 0 to 30 mole %; n is 1 to 99 mole %; x is 0.1 to 30 mole %; and y is 1 to 99 mole %.

The resulting copolymer can have any suitable molecular weight, such as an average molecular weight ranging from about 10,000 to about 200,000. Suitable free radical initiators for the polymerization reaction include organic peroxides, redox catalysts, and azo compounds which decompose under polymerization conditions to give free radicals.

A variety of methods may be capable of producing a suitable polyvinyl amine copolymer, which may then be crosslinked for use in compositions in accordance with the present disclosure, and as known to those skilled in the art.

The polyvinyl amine copolymer of the instant application includes residues of vinyl amine and vinyl alcohol. In some embodiments, the polyvinyl amine copolymer includes greater than or equal to about 0.5 mol % vinyl amine, and less than or equal to about 99 mol % vinyl amine, based on the total amount of the polyvinyl amine copolymer present. Within this range, in one or more embodiments, the polyvinyl amine copolymer includes greater than or equal to about 1 mol % vinyl amine, greater than or equal to about 2 mol %, greater than or equal to about 3 mol %, greater than or equal to about 4 mol %, greater than or equal to about 5 mol %, greater than or equal to about 6 mol %, greater than or equal to about 7 mol %, greater than or equal to about 8 mol %, greater than or equal to about 9 mol %, greater than or equal to about 10 mol %, greater than or equal to about 15 mol %, greater than or equal to about 20 mol %, greater than or equal to about 25 mol %, greater than or equal to about 30 mol %, greater than or equal to about 35 mol %, greater than or equal to about 40 mol %, greater than or equal to about 45 mol %, or greater than or equal to about 50 mol % polyvinyl amine, based on the total amount of the polyvinyl amine copolymer present.

Also within this range, in some embodiments, the polyvinyl amine copolymer includes less than or equal to about 90 mol % vinyl amine, less than or equal to about 80 mol %, less than or equal to about 70 mol %, less than or equal to about 60 mol %, less than or equal to about 50 mol %, less than or equal to about 30 mol %, less than or equal to about 25 mol %, less than or equal to about 20 mol %, less than or equal to about 15 mol %, less than or equal to about 10 mol %, less than or equal to about 9 mol %, less than or equal to about 8 mol %, less than or equal to about 7 mol %, less than or equal to about 6 mol %, less than or equal to about 5 mol %, less than or equal to about 4 mol %, preferably less than or equal to about 3 mol %, or less than or equal to about 2 mol % polyvinyl amine, based on the total amount of the polyvinyl amine copolymer present.

In one or more embodiments, the weight average molecular weight of the polyvinyl amine copolymer may be greater than or equal to about 5,000 g/mol, and less than or equal to about 2,000,000 g/mol. Within this range, in some embodiments, the weight average molecular weight of the polyvinyl amine copolymer is greater than about 10,000, greater than about 20,000, greater than about 30,000, greater than about 40,000, greater than about 50,000, greater than about 60,000, greater than about 70,000, greater than about 80,000, greater than about 90,000, greater than about 100,000, or greater than about 150,000 g/mol.

Also within this range, in some embodiments, the weight average molecular weight of the polyvinyl amine copolymer may be less than about 1,500,000, less than about 1,000,000, less than about 500,000, less than about 100,000, less than about 90,000, less than about 80,000, less than about 70,000, less than about 60,000, less than about 50,000, less than about 40,000, or less than about 20,000 g/mol.

The instant polyvinyl amine copolymer may have an essentially unimodal molecular weight distribution, which may be characterized in a number of ways known to those with ordinary skill in the art.

In one or more embodiments, the polyvinyl amine copolymer may have a polydispersity, determined as the weight average molecular weight (Mw) divided by the number average molecular Weight (Mn) of from 1 to about 200. Within the range, in some embodiments, the polyvinyl amine copolymer may have a polydispersity of greater than or equal to about 2, greater than or equal to about 3, greater than or equal to about 4, greater than or equal to about 5, greater than or equal to about 6, greater than or equal to about 7, greater than or equal to about 8, greater than or equal to about 9, greater than or equal to about 10, greater than or equal to about 15, greater than or equal to about 20, greater than or equal to about 25, greater than or equal to about 30, greater than or equal to about 35, or greater than or equal to about 40.

Also within this range, in some embodiments, the polyvinyl amine copolymer may have a polydispersity of less than or equal to about 45, less than or equal to about 40, less than or equal to about 35, less than or equal to about 30, less than or equal to about 25, less than or equal to about 20, less than or equal to about 15, less than or equal to about 10, less than or equal to about 9, less than or equal to about 15, less than or equal to about 8, less than or equal to about 7, less than or equal to about 6, less than or equal to about 5, or less than or equal to about 4.

Hair Care Compositions

It is commonly understood that untreated hair has an overall negatively charged surface. The polyvinyl amine copolymer discussed above may have a variable charge density owing to the presence of the amine groups on the copolymer. For example, the pH value of a composition including a polyvinyl amine copolymer will determine the degree to which the amine groups of the polymer are protonated or positively charged. The degree of protonation of the amine groups on the polyvinyl amine copolymer, and thus the overall cationic character and charge density of the polyvinyl amine copolymer, may be readily tailored using pH adjustments to modulate the pH above or below the isoelectric point for the polyvinyl amine copolymer.

The isoelectric point is the pH at which a particular molecule carries no net electrical charge. At a pH below their isoelectric point a plurality of molecules (or amine groups attached to a polymer backbone) will have a net positive (cationic) charge, which may increase in degree the further below the isoelectric point the pH is adjusted due to equilibrium considerations. Thus, in some embodiments, the hair care compositions including a polyvinyl amine copolymer of the present disclosure may have a pH value below the isoelectric point of the amine groups of the polyvinyl amine copolymer to ensure that it is cationically charged. The cationic charge may assist in the deposition of the polyvinyl amine copolymer onto the surface of negatively charged untreated hair via an electrostatic attraction.

However, pH values can also affect the swelling and permeability of hair, with pH values of greater than about 8 substantially swelling hair and pH values of greater than about 9.5 capable of even greater swelling of hair. Upon swelling, hair's permeability increases, which may lead to greater penetration and deposition of the polyvinyl amine copolymer and/or a dye onto the hair, among other hair care products that may be applied. Additionally, an increase in hair's permeability not only may result in more deposition of product thereon, but also easier removal of the product during washing. Thus a careful balance of the pH values in the hair care compositions may need to be found, specifically between achieving a favorable cationic charge on the polyvinyl amine copolymer and sufficiently swelling the hair to achieve favorable hair swelling. In one or more embodiments, the pH of the hair care composition may be from about 6 to 12. In more specific embodiments, the pH of the hair care composition may be from about 8 to about 11.5. In even more specific embodiments, the pH of the hair care compositions may be from about 9 to 11. In even more specific embodiments, the pH of the hair care compositions may be from about 9.5 to 10.5. These pH ranges may be particularly effective because they balance the electrostatic attraction of the dye to the hair along with providing sufficient swelling of the hair. Specifically, one would expect to see better dye adhesion to the hair at lower pH values if electrostatic forces alone were driving the adhesion because the amine would be more highly charged at lower pH values. Thus, these pH values may be particularly notable with respect to hair dye oriented hair care compositions because they are commonly formulated to be acidic rather than alkaline.

In one or more embodiments, the polyvinyl amine copolymer may be dissolved in a base fluid to make a hair care composition. In some embodiments, the base fluid may include water and/or a water miscible solvent. The water miscible solvent may include ethanol, isopropyl alcohol, or other known water miscible solvents. It should be understood that the amount of water miscible solvent used in a particular application may depend on the relative solubility of the specific polyvinyl amine copolymer used and its concentration in the hair care composition among many other possible factors. In one or more embodiments, the base fluid may include from about 0.1 to 2.5% by weight water miscible solvent, or from about 0.5 to 5% by weight water miscible solvent, or from about 1 to 10% by weight water miscible solvent. In one or more embodiments, the hair care composition may include at least about 10% by weight base fluid, or at least about 25% by weight base fluid, or at least about 35% by weight base fluid. In one or more embodiments, the hair care composition may include at most about 99% by weight base fluid, at most 95% by weight base fluid, and at most 90% by weight base fluid.

In some embodiments, the polyvinyl amine copolymer may be applied to the hair as a pre-treatment to render the hair more amenable to a subsequent hair care product application (e.g., hair dye, hair spray, conditioning agent, etc.). In other embodiments, the polyvinyl amine copolymer may be included within a fully formulated hair care composition to improve the properties thereof. Whether as a pre-treatment or in a fully formulated product, the amount of polyvinyl amine copolymer present in the applied hair care composition may be up to about 10% by weight, or up to about 5% by weight, or up to about 1% by weight, or up to about 0.5% by weight, or up to about 0.25% by weight of the hair care composition. In one or more embodiments, the amount of polyvinyl amine copolymer present in the applied hair care composition may be at least about 0.01% by weight, or at least about 0.05% by weight, or at least about 0.075% by weight, or at least about 1.5% by weight, or at least about 2.5% by weight of the hair care composition.

In one or more embodiments, the hair care composition is a hair dye pre-treatment composition that is applied to the hair prior to the application of a dye/colorant composition. In other embodiments, the hair care composition is a fully formulated hair dye composition, meaning the polyvinyl amine copolymer is included and mixed directly within a single hair care composition along with the dye/colorant, aqueous base fluid, and any other additives that may be present. In some embodiments, the fully formulated hair dye composition includes an anionic or a cationic dye. For example, a fully formulated hair dye composition may include an anionic or cationic dye. In one or more embodiments, the anionic or cationic dye may include at least one selected from Direct Red 80, Basic Blue 3, acid violet 43, D&C Orange 5, disperse black 9, and Fast Green ECF. In one or more embodiments, the dye/colorant may be included in an amount from about 0.05 to 10% by weight, or from about 0.75 to 7.5% by weight or from about 0.1 to 5% by weight. In addition, other additives that may be included in a fully formulated hair dye composition may include conditioners, buffers, thickening agents, compatibilizers, emulsifiers, suspending agents, and color enhancers Advantageously, it has been found that the inclusion of a polyvinyl amine copolymer, either as a pre-treatment composition or as a component of a fully formulated product hair dye product, in a hair dye regimen may improve the initial color intensity of the dyed hair and also may improve the washfastness of the dye. That is to say, the polyvinyl amine copolymer may facilitate the deposition of the dye onto the hair evenly and in significant amounts and that the dye may be retained better on the hair after washing maintaining sufficient color intensity throughout multiple washings when using the polyvinyl amine copolymer. These high performance characteristics will be shown and explained more completely in the examples presented below.

EXAMPLES

Rubine Dye Test

The Rubine Dye Test was utilized to demonstrate the amount of polyvinyl amine copolymer that may be deposited onto keratonic substrates. Briefly, in the Rubine Dye Test a cationic polymer may be applied to a keratonic substrate where it adheres to the negatively charged keratonic substrate, then an anionic dye may be applied to the cationic polymer coated keratonic substrate and an amount of the anionic dye may interact with the cationic polymer and adhere to the cationic polymer coated keratonic substrate. A color reading may then be taken of the keratonic substrate to determine the amount of anionic dye adhered thereto, which may then be correlated to the amount of cationic polymer present on the hair (e.g., the more intense the color then the more cationic polymer was deposited onto the keratonic substrate). FIG. 1 shows a graphical illustration of the general steps in a Rubine Dye Test.

The specific procedure used for the Rubine Dye Test results described herein is as follows. First, the keratonic substrate(s) was washed with a 10% sodium lauryl ether sulfate (SLES) solution, which is a detergent and is used to cleanse the keratonic substrates. After rinsing the SLES from the keratonic substrates in warm water, the keratonic substrates(s) are then submersed and soaked in a solution of cationic polymer for five minutes. After a rinsing cycle in warm water for 60 seconds to remove the non-attached cationic polymer from the cationic polymer modified keratonic substrates, the cationic polymer modified keratonic substrates are then submersed and soaked in a solution of anionic dye for five minutes. The keratonic substrates are then rinsed again with warm water and dried to create a dyed keratonic substrate. When needed, the pH of the solutions used above were adjusted to the detailed value with solutions of either 1% NaOH or 1% HCl. After drying, the samples were compared visually and quantitatively with a colorimeter. The colorimeter readings were taken with a Brightmeter Micro S-5 available from Technidyne Corp. Where reported, the data is at the 95% confidence interval.

Rubine Dye Test on Virgin Blonde Hair

Figure 2:
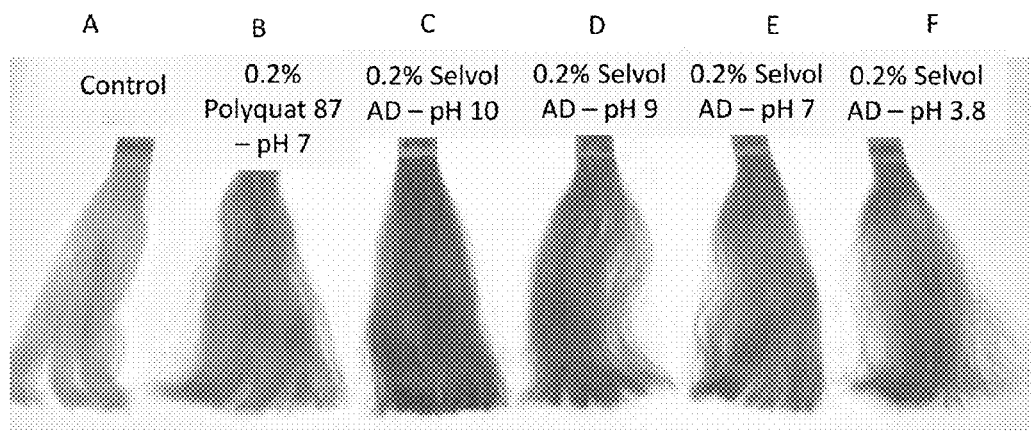
FIG. 2 is a color photograph showing a comparison of hair samples A-F subjected to a Rubine Dye Test under different conditions, wherein A is an image of virgin blonde hair after the performance of a Rubine Dye Test using no cationic polymer;
B is an image of virgin blonde hair after being subjected to a Rubine Dye Test at a pH of 7 using 0.2% Polyquat 87 as a cationic polymer;
C is an image of virgin blonde hair after being subjected to a Rubine Dye Test at a pH of 10 using 0.2% Selvol AD as a cationic polymer;
D is an image of virgin blonde hair after being subjected to a Rubine Dye Test at a pH of 9 using 0.2% Selvol AD as a cationic polymer;
E is an image of virgin blonde hair after being subjected to a Rubine Dye Test at a pH of 7 using 0.2% Selvol AD as a cationic polymer; and
F is an image of virgin blonde hair after being subjected to a Rubine Dye Test at a pH of 3.8 using 0.2% Selvol AD as a cationic polymer.

FIG. 2 shows images of the results of a Rubine Dye Test performed on virgin blonde hair (purchased from International Hair Importers and Products, Glendale, N.Y.) using either no cationic polymer (the control), Selvol™ AD or polyquaternium (polyquat) 87 as the cationic polymers. Selvol™ AD is a polyvinyl amine copolymer that possesses roughly 5-11 mol % amine group functionality that is available from Sekisui Specialty Chemicals, while polyquat-87 is a common commercial cationic polymer that is available from, among others, BASF as Luviquat® Sensation. The anionic dye used in these experiments was Direct Red 80. Additionally, FIG. 2 shows the effect that changing the pH value of the wash/soak solutions has on the hair samples treated with the Selvol AD. In FIG. 2, the Selvol™ AD shows a marked improvement in the color intensity (e.g., a darker coloration) over the control and the polyquat-87 treated at the same pH. FIG. 2 also shows that the color intensity when using the Selvol™ AD is a function of solution pH value, with the color intensity decreasing as the value is decreased. Without being bound by theory, the improvement in color intensity shown in FIG. 2 as a function of increasing pH may be correlated to the hair permeability increasing as the pH increases, allowing the polyvinyl amine copolymer and subsequently the dye to more readily penetrate and dye the hair, as discussed above.

Figure 3:
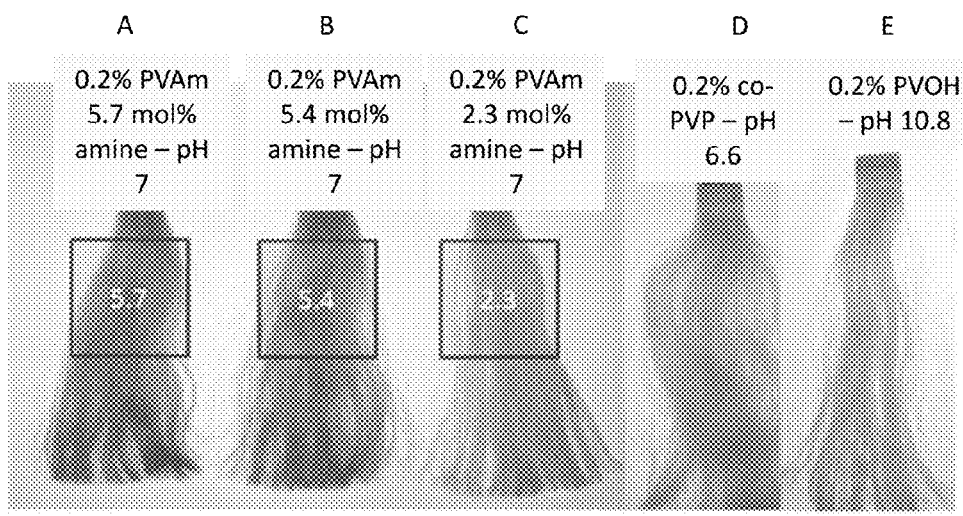
FIG. 3 is a color photograph showing a comparison of additional hair samples A-E subjected to a Rubine Dye Test under different conditions, wherein A is an image of virgin blonde hair after being subjected to a Rubine Dye Test at a pH of 7 using a 0.2% polyvinyl amine copolymer solution, wherein the polyvinyl amine copolymer has 5.5-6 mol % amine residues;
B is an image of virgin blonde hair after being subjected to a Rubine Dye Test at a pH of 7 using a 0.2% polyvinyl amine copolymer solution, wherein the polyvinyl amine copolymer has 5-5.4 mol % amine residues;
C is an image of virgin blonde hair after being subjected to a Rubine Dye Test at a pH of 7 using a 0.2% polyvinyl amine copolymer solution, wherein the polyvinyl amine copolymer has 2-2.5 mol % amine residues;
D is an image of virgin blonde hair after being subjected to a Rubine Dye Test at a pH of 6.6 using a 0.2% vinyl pyrrolidone vinyl alcohol copolymer containing 5 mol % vinyl pyrrolidone; and
E is an image of virgin blonde hair after being subjected to a Rubine Dye Test at a pH of 10.8 using a 0.2% polyvinyl alcohol homopolymer solution.

FIG. 3 shows images of the results of another Rubine Dye Test performed on virgin blonde hair. The anionic dye used in these experiments was Direct Red 80. In this test, a polyvinyl alcohol polyvinyl amine copolymer (PVAm) containing differing amount of amine functionality were tested in addition to a vinyl alcohol vinyl pyrollidone copolymer (co-PVP) with 5 mol % PVP and a polyvinyl alcohol homopolymer. In all the samples tested a concentration of 0.2 weight percent polymer was used. The results presented in FIG. 3 show that for a given cationic polymer a higher cationic charge density (i.e., more cationic groups) leads to more deposition of the cationic polymer onto the hair. For example, the coloration of the left two samples is much darker than the third sample treated with polyvinyl amine copolymer having a smaller amount of amine functionality. Indeed, the sample treated with polyvinyl amine copolymer having the least amount of amine functionality showed only slightly more color intensity than the sample treated with the polyvinyl alcohol that does not possess amine groups (PVOH) and the polyvinyl alcohol copolymer that has nitrogen groups that are not capable of being positively charged (co-PVP). The PVOH and co-PVP containing examples are used to show that when the polymer is not charged there is little to no dye adhesion.

Rubine Dye Test on Wool Swatches

Figure 4:
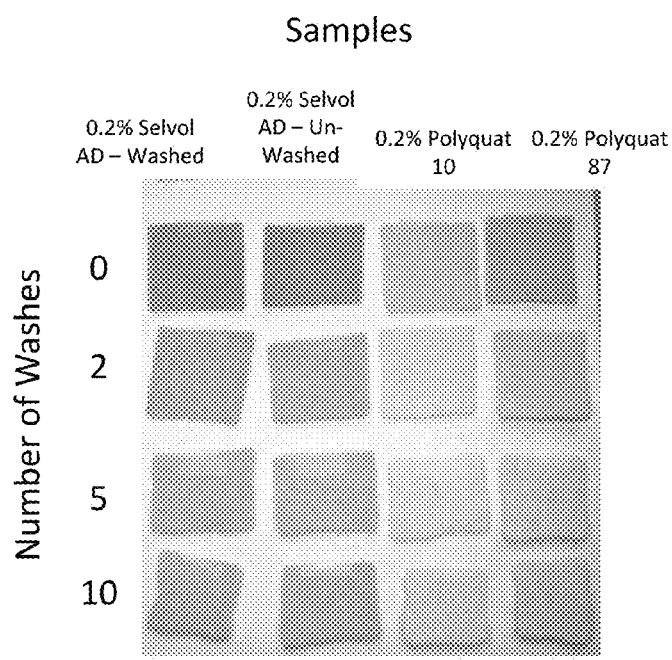
FIG. 4 shows images of wool swatches after being subjected to a Rubine Dye Test using different cationic polymers and also after 0, 2, 5, or 10 washings.

FIG. 4 shows images of the results of a Rubine Dye Test performed on wool swatches treated with different cationic polymers and also after various amounts of washings. The anionic dye used in these experiments was Direct Red 80. In this test, the values on the left axis indicate how many washes with a 10% SLES solution that the dyed wool swatches have been subjected to. The two samples on the left were treated with Selvol™ AD having about 8 mol % amine, with the leftmost "washed" sample having the Selvol™ AD washed to remove any residual base or salts prior to the suspension/soak in the polyvinyl amine copolymer, while the other sample was suspended/soaked directly in the polyvinyl amine copolymer with no pre-wash. The two samples on the right were both suspended/soaked in a polyquaternium polymer, with the rightmost sample being treated with polyquat-87 and the other sample being treated with polyquat-10. A structural difference between polyquat-87 and polyquat-10 is that polyquat-10 has a much lower molecular weight. Polyquat-87 has a molecular weight from about 100-180 kDa, while polyquat-10 has a molecular weight from about 3-30 kDa. The larger polyquat-87 has more quaternium centers than the polyquat-10 and thus has a higher cationic charge density of 3.7-5.2 meq/g (depending on the pH) versus 1.0-2.0 meq/g (depending on the pH) for polyquat-87. The Selvol™ AD has a molecular weight similar to polyquat-10 but a cationic charge density of 1.7-2.3 meq/g (depending on amine loading and pH), both of which are more closely aligned with polyquat-10.

FIG. 4 visually shows that the polyvinyl amine copolymer treated wool swatches displayed a greater color intensity (e.g., a darker coloration) than the wool swatches treated with the polyquaternium cationic polymers, with very little difference visually between the pre-washed polymer and non-washed polymer treated swatches, indicating that the amine groups on the copolymer and not residual salts or other contaminant species in the unwashed polymer are what is driving the dye uptake. The increased color intensity for the wool swatches treated with the polyvinyl amine copolymer compared to polyquat 87 indicates that charge density is not the only factor contributing to dye uptake. Further, by retaining their color better after washing cycles, the polyvinyl amine copolymer treated wool swatches display a superior washfastness when compared to the polyquaternium cationic polymers, which lost most of their color after only 5 washes. Interestingly, when comparing the polyquaternium cationic polymers, it is shown that the wool swatches treated with polyquat-87 display a greater color intensity initially than the polyquat-10, although the color intensity substantially equalizes after about 5 washes, indicating that increases in molecular weight and charge density may lead to the deposition or attachment of more anionic dye initially but will not lead to increased retention of the dye after wash cycles.

Figure 5:
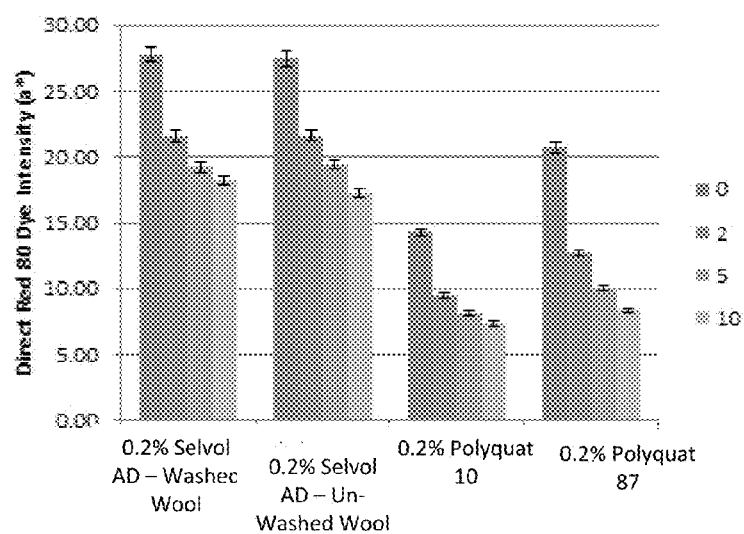
FIG. 5 shows a plot of the quantitative results obtained from colorimetrically testing the wool swatches shown in FIG. 4.

FIG. 5 shows a plot of the quantitative results from the colorimetric testing (a* value) for the wool swatches shown in FIG. 4. By examining the data, it is easy to confirm the general trends discussed above for FIG. 4. More specifically, the polyvinyl amine copolymer treated wool swatches show an approximately 20% greater initial color intensity than the polyquat-87 treated swatches and an approximately 60% greater initial color intensity than the polyquat-10 treated swatches. Further, an even larger color intensity difference is seen relative to polyquat-87 and polyquat-10 after multiple washings with a 10% SLES solution. Without being bound by theory, it is believed that the improved washfastness of the polyvinyl amine copolymer treated wool swatches is due to the polyvinyl amine copolymer binding more strongly to the wool swatches than the polyquaternium polymers.

In order to better understand the impact of the molecular weight and charge density of the cationic molecules that may be used to pre-dye treatment during the Rubine Dye Test a systematic study on wool swatches was done with a variety of cationic molecules. In this study polyquat-10, polyquat-87 were tested, along with two common cationic conditioning agents having much lower molecular weights, stearyl alkonium chloride (SAC) and cetyl trimethyl ammonium chloride (CTAC). Table 1 shows the results of these studies. The solutions of cationic molecules used to treat the wool swatches each contained 0.2 weight % of the cationic molecules. Each a* value in the table is the average result of multiple trials. The "One Wash" a* value is the value after washing the initially dyed wool swatch with a 10% SLES solution.

TABLE 1

| Pre-Dye Treatment | pH | Charge Density (meq/g) | Molecular Weight - $M_w$ (Da) | Initial a* | One Wash a* | % Color Loss |
|---|---|---|---|---|---|---|
| DI Water | 6.5 | 0 | N/A | 12.3 | 8.8 | 28.5 |
| Polyquat-10 | 6-6.5 | 1 | ~100,000 | 17.3 | 13.8 | 19.8 |
| Polyvinyl amine copolymer | 10.2 | 1.5-1.9 | ~20,000 | 29 | 25 | 13.8 |
| SAC | 6-6.5 | 2.4 | 424 | 27.6 | 7.3 | 73.6 |
| CTAC | 5-6 | 3.1 | 320 | 42.8 | 9.7 | 77.3 |
| Polyquat-87 | 6.5-7 | 3.7 | ~250,000 | 25 | 16.8 | 32.8 |

Table 1 shows that the common cationic conditioning agents, SAC and CTAC, have the highest color intensity before the washing. However, after one wash, the majority of the dye washes off of the wool swatches as indicated by their high color loss percentages. The low washfastness for these non-polymeric molecules likely results because they are not bound strongly to the hair and are easily removed during the washing. As previously discussed, the polyvinyl amine copolymer shows higher than expected initial color intensity (based on its charge density), while also exhibiting the lowest color loss percentage after the initial wash. The high pH value used for the polyvinyl amine copolymer is thought to increase the color intensity by causing the hair to swell, but that does not completely explain the initial color intensity or the high degree of washfastness observed for the polyvinyl amine copolymer treated swatches.

For example, Table 2 shows data tracking the change in the initial color intensity (a*) for wool swatches treated with 0.2 wt. % polyvinyl amine copolymers when varying the pH value during their treatment.

TABLE 2

| pH | Initial a* |
|---|---|
| 11.2 | 30 |
| 10.2 | 29 |
| 9.4 | 28.5 |
| 7.2 | 26.02 |
| 3.66 | 22.2 |

Figure 6:
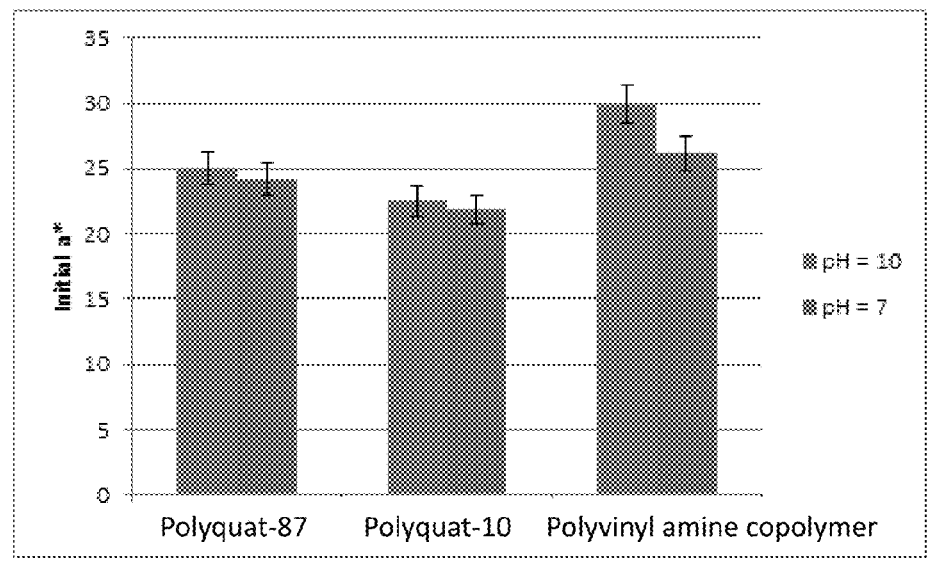
FIG. 6 is plot comparing the initial a* values for keratonic substrates dyed using the Rubine Dye Test with different cationic polymers and depending upon the pH.

As expected due to the swelling of the hair at higher pH, the color intensity increases as the pH increases. However, the color intensity at around neutral pH (~7) compares very favorably with the value seen in Table 1 for polyquat-87 and is significantly greater than the value seen for polyquat-10. FIG. 6 shows that the initial color intensity (a*) values for the polyquat-10 and polyquat-87 when applied at higher pH-values do not rival that of the polyvinyl amine copolymer (all samples with 0.2% wt. % polymer), and remains very similar to their values when applied at neutral pH. Without being bound by theory, it is believed that the unexpectedly high initial color intensity and washfastness imparted to the keratonic substrates through their treatment with the polyvinyl amine copolymer may be explained in that the relatively smaller molecular weight of the polymer when compared to polyquat-10 and polyquat-87 may allow it to more readily penetrate the keratonic substrates upon their swelling at higher pH values, where it then forms a film on the surface. Because the polyvinyl amine copolymer may penetrate more deeply into the keratonic substrate it may maintain a more substantive film thereon. Thus, after the dye is applied to the swelled and treated keratonic substrate, the dye may be more effectively trapped and retained upon the shrinking of the keratonic substrate when it is dried. Accordingly, the washfastness of the dye may be improved by trapping a significant amount of the dye within the polyvinyl amine treated keratonic substrate.

Figure 7:
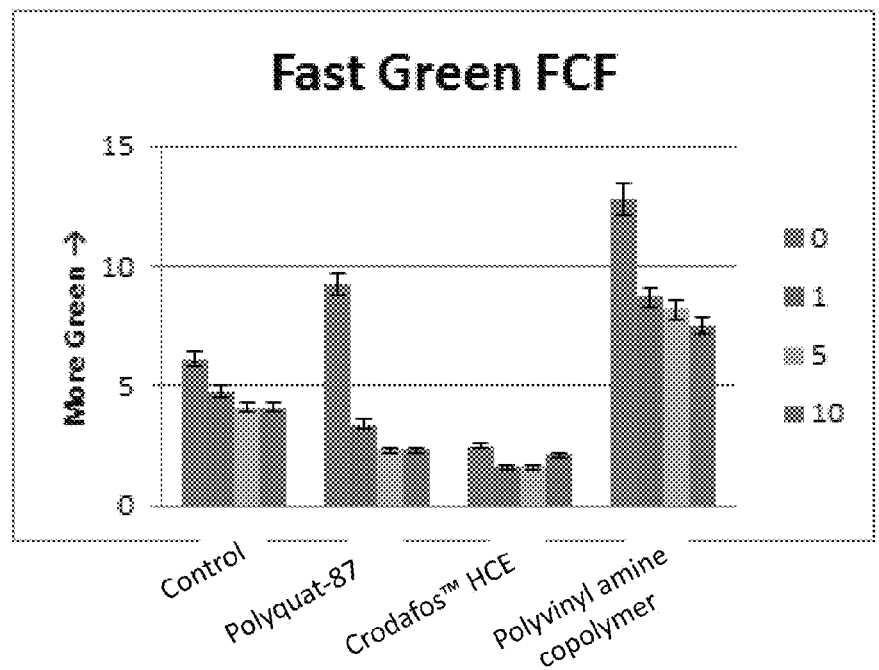
FIG. 7 shows a plot of the quantitative results obtained from colorimetrically testing wool swatches subjected to a Rubine Dye Test using Fast Green FCF as a dye.

The above described effect of unexpectedly high color intensity and washfastness when using a polyvinyl amine copolymer has been shown when other anionic dyes are used in place of the Direct Red 80. For example, FIG. 7 shows a plot of the quantitative results from the colorimetric testing (a* value) for wool swatches subjected to the Rubine Dye Test described above, with the only difference being that the anionic dye used was Fast Green FCF instead of Direct Red 80. Similar to the results shown for the wool swatches shown in FIGS. 4-5, the polyvinyl amine copolymer demonstrated higher levels of color intensity after the initial treatment, providing improved washfastness over the blank, which was a control using no cationic polymer pre-treatment, polyquat-87, and Crodafos™ HCE (an anionic surfactant marketed as a color enhancer for hair dyes that is said to increase color intensity and improve washfastness) when all were used at 0.2 wt. %.

Figure 8:
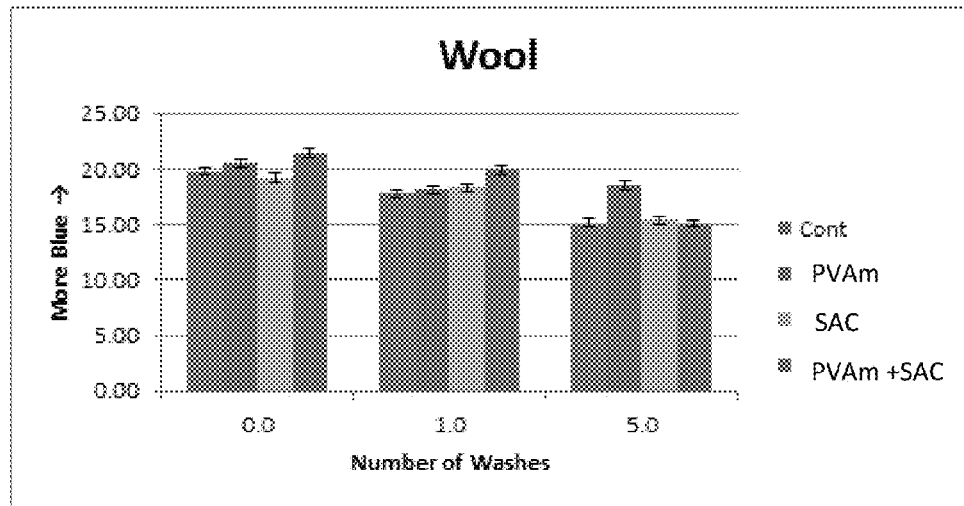
FIG. 8 shows a plot exhibiting the washfastness of wool swatches subjected to a Rubine Dye test using different cationic polymers.
Figure 9:
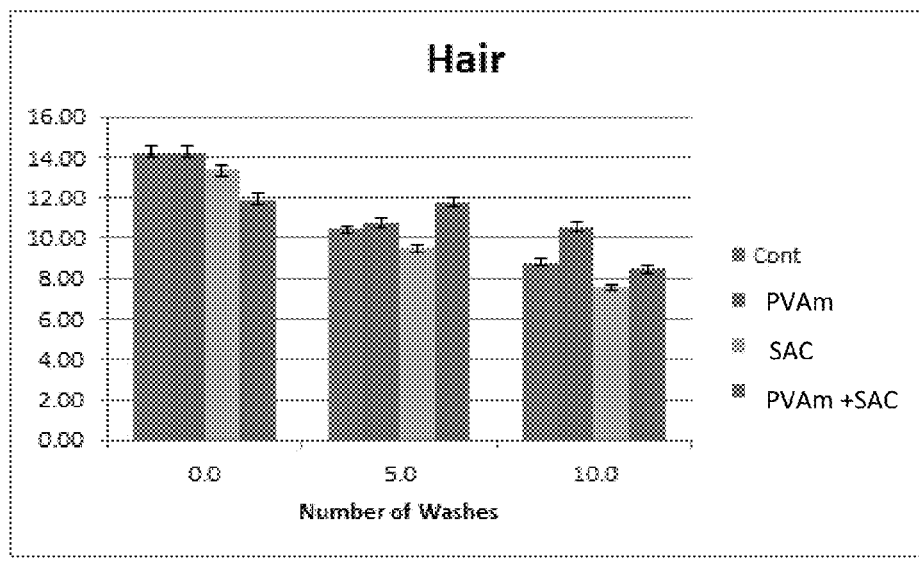
FIG. 9 shows a plot exhibiting the washfastness of virgin blonde hair subjected to a Rubine Dye test using different cationic polymers.

Additionally, and unexpectedly, it was also found that the polyvinyl amine copolymer treatment could improve the washfastness for a fully formulated blue hair dye when used either as a replacement for or, in conjunction with, the multifunctional conditioning agent SAC. For example, FIG. 8 shows that the wool swatch treated only with the polyvinyl amine had superior washfastness after five washes, while the wool swatch treated with both SAC and the polyvinyl amine had superior washfastness after one wash. Further, FIG. 9 demonstrates that on virgin blonde hair, similar results are achieved at ten washes and five washes, respectively. Apart from these examples demonstrating the effectiveness of the polyvinyl amine copolymer in a fully formulated hair dye, these examples are interesting because the blue dye used, Basic Blue 3, is a cationic dye. Thus, the improved washfastness results presented in FIGS. 8-9 demonstrate that the improvement is not just related to electrostatic attraction, but it also likely due to the superior film forming properties of the polyvinyl amine copolymer on the swelled keratonic substrates. Accordingly, the treatment of keratonic substrates with polyvinyl amine copolymer may be effectively used to achieve superior color intensity and washfastness for a variety of dye formulations. Furthermore, the potential to replace SAC and CTAC with the polyvinyl amine copolymer in a fully formulated dye is significant because SAC and CTAC are expensive ingredients that formulators would be interested in replacing if the same or superior properties may be achieved by the cheaper replacement.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims.

What is claimed:
1. A method for dyeing hair, comprising:
applying a polyvinyl amine copolymer solution to the hair, wherein the polyvinyl amine copolymer comprises from about 0.5 mol % to 20 mol % amine functional groups; and
applying a hair dye composition to the hair, wherein the polyvinyl amine copolymer solution is applied to the hair prior to the hair dye composition.

2. The method for dyeing hair of claim 1, wherein applying the polyvinyl amine copolymer solution to the hair comprises:
spraying the polyvinyl amine copolymer solution onto the hair.

3. The method for dyeing hair of claim 1, wherein the weight average molecular weight of the polyvinyl amine copolymer is greater than or equal to about 5,000 g/mol, and less than or equal to about 2,000,000 g/mol.

4. The method for dyeing hair of claim 1, wherein the polyvinyl amine copolymer solution has a pH value from about 6 to 12.

5. The method for dyeing hair of claim 1, wherein the amount of polyvinyl amine copolymer within the polyvinyl amine copolymer solution is from about 0.01% to 10% by weight of the solution.

6. The method for dyeing hair of claim 1, wherein the hair dye composition includes an anionic or a cationic hair dye.

7. The method for dyeing hair of claim 6, wherein the anionic or cationic hair dye is at least one selected from Direct Red 80, Basic Blue 3, acid violet 43, D&C Orange 5, disperse black 9, and Fast Green FCF.

8. A method for dyeing hair, comprising:
applying a polyvinyl amine copolymer solution to the hair, wherein the weight average molecular weight of the polyvinyl amine copolymer is greater than or equal to about 5,000 g/mol, and less than or equal to about 2,000,000 g/mol; and
applying an anionic or cationic hair dye composition to the hair, wherein the polyvinyl amine copolymer solution is applied to the hair prior to the hair dye composition.

9. The method for dyeing hair of claim 8, wherein the polyvinyl amine copolymer comprises from about 0.5 mol % to 20 mol % amine functional groups.

10. The method for dyeing hair of claim 8, wherein the polyvinyl amine copolymer solution has a pH value from about 6 to 12.

11. The method for dyeing hair of claim 8, wherein the amount of polyvinyl amine copolymer within the polyvinyl amine copolymer solution is from about 0.01% to 10% by weight of the solution.

12. The method for dyeing hair of claim 8, wherein the anionic or cationic hair dye is at least one selected from Direct Red 80, Basic Blue 3, acid violet 43, D&C Orange 5, disperse black 9 and Fast Green FCF.

13. The method for dyeing hair of claim 8, wherein the hair dye composition further comprises:

at least one additive selected from a conditioner, buffer, thickening agent, color enhancer, compatibilizer, emulsifier, and suspending agent.

14. A method for dyeing hair, comprising:

applying a polyvinyl amine copolymer solution to the hair, wherein the polyvinyl amine copolymer solution has a pH value of from about 6 to 12; and applying a hair dye composition to the hair, wherein the polyvinyl amine copolymer solution is applied to the hair prior to the hair dye composition.

* * * * *